US012593996B2

(12) United States Patent
Shimuta

(10) Patent No.: US 12,593,996 B2
(45) **Date of Patent: \*Apr. 7, 2026**

(54) PULSE WAVE TRANSIT TIME MEASUREMENT DEVICE AND LIVING BODY STATE ESTIMATION DEVICE

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Kyoto (JP)

( \* ) Notice: Subject to any disclaimer, the term of this patent is extended or adjusted under 35 U.S.C. 154(b) by 907 days.

This patent is subject to a terminal disclaimer.

(21) Appl. No.: 15/979,575

(22) Filed: May 15, 2018

(65) Prior Publication Data

US 2018/0256048 A1 Sep. 13, 2018

Related U.S. Application Data

(63) Continuation of application No. PCT/JP2016/080797, filed on Oct. 18, 2016.

(30) Foreign Application Priority Data

Nov. 17, 2015 (JP) ................................. 2015-225210

(51) Int. Cl.
*A61B 5/024* (2006.01)
*A61B 5/00* (2006.01)
(Continued)

(52) U.S. Cl.
CPC ...... *A61B 5/02427* (2013.01); *A61B 5/02125* (2013.01); *A61B 5/1071* (2013.01);
(Continued)

(58) Field of Classification Search
None
See application file for complete search history.

(56) References Cited

U.S. PATENT DOCUMENTS 5,941,837 A * 8/1999 Amano ................. A61B 5/024
600/595
6,030,342 A * 2/2000 Amano ................ A61B 5/4866
600/549
(Continued)

FOREIGN PATENT DOCUMENTS

JP 10-309266 A 11/1998
JP 2001-161649 A 6/2001
(Continued)

OTHER PUBLICATIONS

Ikeda, Shiho, Hitoshi Ishimura, and Masafumi Matsumura. "Nonrestrictive measurement of pulse transit time using ECG sensor and PPG sensor mounted on the neckband." Transactions of Japanese Society for Medical and Biological Engineering 51. Supplement (2013): R-2. (Year: 2013).*

(Continued)

*Primary Examiner* — Jacqueline Cheng
*Assistant Examiner* — Jairo H Portillo
(74) *Attorney, Agent, or Firm* — Keating & Bennett, LLP

(57) ABSTRACT

A pulse wave transit time measurement device includes a neck band, a pair of electrocardiographic electrodes detecting an electrocardiographic signal, a photoplethysmographic sensor detecting a pulse wave signal, and a pulse wave transit time calculator calculating a pulse wave transit time based on a peak time difference between the electrocardiographic signal detected by the electrocardiographic electrodes and the pulse wave signal detected by the photoplethysmographic sensor. The photoplethysmographic sensor is positioned in or substantially in a central region of the neck band at a location at which the photoplethysmographic (Continued)

sensor is in contact with a neck of a user at or near a midline of the neck on the backside when the neck band is worn around the neck of the user.

18 Claims, 5 Drawing Sheets

(51) Int. Cl.

| | |
|---|---|
| *A61B 5/021* | (2006.01) |
| *A61B 5/107* | (2006.01) |
| *A61B 5/11* | (2006.01) |
| *A61B 5/282* | (2021.01) |
| *A61B 5/346* | (2021.01) |
| *A61B 5/022* | (2006.01) |
| *A61B 5/145* | (2006.01) |
| *A61B 5/352* | (2021.01) |

(52) U.S. Cl.

CPC ............ *A61B 5/1116* (2013.01); *A61B 5/282* (2021.01); *A61B 5/346* (2021.01); *A61B 5/6822* (2013.01); *A61B 5/6831* (2013.01); *A61B 5/721* (2013.01); *A61B 5/0022* (2013.01); *A61B 5/022* (2013.01); *A61B 5/02444* (2013.01); *A61B 5/14542* (2013.01); *A61B 5/352* (2021.01); *A61B 5/7264* (2013.01); *A61B 5/7278* (2013.01); *A61B 2560/0204* (2013.01); *A61B 2560/0223* (2013.01); *A61B 2562/0204* (2013.01); *A61B 2562/0219* (2013.01); *A61B 2562/0271* (2013.01); *A61B 2562/029* (2013.01)

(56) References Cited

U.S. PATENT DOCUMENTS

| | | | | |
|---|---|---|---|---|
| 6,081,742 | A * | 6/2000 | Amano ................ | A61B 5/0205 600/484 |
| 6,836,680 | B2 * | 12/2004 | Kuo ..................... | A61B 5/4035 600/513 |
| 8,718,980 | B2 * | 5/2014 | Garudadri ............ | A61B 5/0002 702/189 |
| 2001/0003792 | A1 | 6/2001 | Ogura et al. | |
| 2004/0210155 | A1 * | 10/2004 | Takemura ........... | A61B 5/0064 600/534 |
| 2005/0234351 | A1 | 10/2005 | Nishii et al. | |
| 2006/0200011 | A1 | 9/2006 | Suzuki et al. | |
| 2007/0032711 | A1 * | 2/2007 | Coakley ............... | A61B 5/6826 600/323 |
| 2007/0083125 | A1 | 4/2007 | Ouchi et al. | |
| 2007/0142715 | A1 * | 6/2007 | Banet ................. | A61B 5/14552 600/323 |
| 2009/0082699 | A1 * | 3/2009 | Bang ................. | G06K 9/00342 600/595 |
| 2014/0187941 | A1 * | 7/2014 | Shusterman ............. | A61B 8/04 600/438 |
| 2014/0236027 | A1 * | 8/2014 | Banet ................... | A61B 5/6822 600/484 |
| 2014/0236037 | A1 * | 8/2014 | Banet ................... | A61B 5/1126 600/536 |
| 2015/0164437 | A1 * | 6/2015 | McCombie ........... | A61B 5/1114 600/301 |
| 2015/0289785 | A1 * | 10/2015 | Bojovic ................. | A61B 5/318 128/204.23 |

FOREIGN PATENT DOCUMENTS

| | | | |
|---|---|---|---|
| JP | 2003-225211 A | 8/2003 | |
| JP | 2005-324004 A | 11/2005 | |
| JP | 2006-212218 A | 8/2006 | |
| JP | 2007-061439 A | 3/2007 | |
| JP | 2007-202939 A | 8/2007 | |
| JP | 2014-000105 A | 1/2014 | |
| WO | WO-2015048502 A1 * | 4/2015 | ............. A61B 5/316 |

OTHER PUBLICATIONS

Official Communication issued in International Patent Application No. PCT/JP2016/080797, mailed on Dec. 27, 2016.

* cited by examiner

PULSE WAVE TRANSIT TIME MEASUREMENT DEVICE AND LIVING BODY STATE ESTIMATION DEVICE

CROSS REFERENCE TO RELATED APPLICATIONS

This application claims the benefit of priority to Japanese Patent Application No. 2015-225210 filed on Nov. 17, 2015 and is a Continuation Application of PCT Application No. PCT/JP2016/080797 filed on Oct. 18, 2016. The entire contents of each application are hereby incorporated herein by reference.

BACKGROUND OF THE INVENTION

1. Field of the Invention

The present invention relates to a pulse wave transit time measurement device that measures a pulse wave transit time, and to a living body state estimation device including the pulse wave transit time measurement device.

2. Description of the Related Art

Recently, a pulse wave transit time representing a time taken for a pulse wave to transit in arteries inside a living body (e.g., a time from an R wave to the appearance of a pulse wave in an electrocardiogram) and reflecting change of blood pressure has been used as an index in, for example, evaluation of arterial stiffness and estimation of a vascular lifetime.

Japanese Unexamined Patent Application Publication No. 2014-105 discloses a technique of calculating a systolic blood pressure from a pulse wave transit time (i.e., a noninvasive continuous blood-pressure monitoring device). According to the disclosed technique, the pulse wave transit time is determined from both a pulse wave signal that is obtained by a photoplethysmographic sensor (such as an earlobe photoplethysmographic sensor or a fingertip photoplethysmographic sensor) set on the earlobe or the fingertip of a subject, and an electrocardiographic signal that is obtained by an ECG sensor set on the subject, and the systolic blood pressure is calculated by using the determined pulse wave transit time and a blood pressure calculation formula. In addition, according to the disclosed technique, not only fluctuations in blood pressure, but also a posture and a motion of the subject are able to be monitored at the same time by setting a 3-axis acceleration detection sensor on the subject, detecting the posture and the motion of the subject from detected data, and by simultaneously obtaining blood pressure data and motion data of the subject in the time series.

Japanese Unexamined Patent Application Publication No. 2001-161649 discloses a pulse-wave transit time (velocity) information measurement device with which precise pulse-wave transit time (velocity) information is able to be acquired by detecting a branch location of a carotid artery present under the skin, and by detecting a pulse wave from a constant detection position that has been determined on the basis of the detected branch point. When acquiring the pulse wave transit time information with the pulse-wave transit time (velocity) information measurement device, a pulse wave detection sensor that detects a carotid artery pulse wave corresponding to pressure change within the carotid artery is first placed on the carotid artery using a band wearable on the neck of a living body. The carotid artery includes a common carotid artery and a pair of inner carotid artery and outer carotid artery branching from the common carotid artery. The pulse wave detection sensor is set such that its pressing surface presses the branch location (branch point) at which the pair of inner carotid artery and outer carotid artery branch from the common carotid artery. When the pulse-wave detection position for the artery is determined on the basis of the branch point of the carotid artery, a reference point for a pressure pulse wave obtained from the pulse-wave detection position is determined, and the pulse wave transit time information is calculated on the basis of the reference point for the pressure pulse wave.

According to the technique (noninvasive continuous blood-pressure monitoring device) disclosed in Japanese Unexamined Patent Application Publication No. 2014-105, as described above, not only the fluctuations in the blood pressure (fluctuations in the pulse wave transit time), but also the posture and the motion of the subject are able to be monitored at the same time by calculating the blood pressure from the calculated pulse wave transit time while concurrently detecting the posture and the motion of the subject. According to the technique (pulse-wave transit time (velocity) information measurement device) disclosed in Japanese Unexamined Patent Application Publication No. 2001-161649, because the pulse-wave detection position is determined on the basis of the branch location of the carotid artery and the pulse wave transit time information is calculated on the basis of the reference point for the pressure pulse wave obtained from the pulse-wave detection position, the pulse-wave detection position on the artery is maintained constant, and thus the pulse wave transit time information is precisely calculated.

A value of the pulse wave transit time changes depending on the posture of the subject (user) and the measurement location. However, that point is not taken into consideration in the technique (noninvasive continuous blood-pressure monitoring device) disclosed in Japanese Unexamined Patent Application Publication No. 2014-105 and the technique (pulse-wave transit time (velocity) information measurement device) disclosed in Japanese Unexamined Patent Application Publication No. 2001-161649. More specifically, although the pulse wave signal is obtained from, for example, the earlobe in the device disclosed in Japanese Unexamined Patent Application Publication No. 2014-105, the pulse wave transit times when the user is in the left and right lateral decubitus positions, for example, are different and a measurement error of the pulse wave transit time is generated depending on whether the pulse wave signal is obtained from the left or right earlobe.

Similarly, although the pulse wave signal is obtained from the carotid artery in Japanese Unexamined Patent Application Publication No. 2001-161649, the pulse wave transit times when the user is in the left and right lateral decubitus positions, for example, are different and a measurement error of the pulse wave transit time is generated depending on whether the pulse wave signal is obtained from the left or right carotid artery. Furthermore, in this case, if the measurement location deviates even slightly from the carotid artery, the measurement location is changed to a zone of capillaries, thus causing a possibility that the amplitude of the pulse wave signal is reduced and a measured value of the pulse wave transit time is also changed. In other words, location dependency is significant. This implies that the measurement location for the pulse wave signal needs to be prevented from deviating from the carotid artery during the measurement of the pulse wave transit time, and that it is difficult to stably perform the measurement. In trying to measure the pulse wave transit time during sleep, for example, there is a possibility that stable measurement cannot be performed if the measurement location is displaced due to, for example, rolling-over during sleep.

Thus, the above-described techniques disclosed in Japanese Unexamined Patent Application Publication No. 2014-105 and Japanese Unexamined Patent Application Publication No. 2001-161649 have the following problem. When the posture of the user is changed during the measurement of the pulse wave transit time (e.g., during sleep) as represented, for example, in the case of continuously measuring the pulse wave transit time for a comparatively long time (e.g., for several hours) and checking a trend of fluctuations in the pulse wave transit time, the measured pulse wave transit time is changed before and after the change of the posture (for example, if the user rolls over in sleep, the measured pulse wave transit time is changed between before and after the rolling-over). Thus, the pulse wave transit time cannot be continuously measured with stability.

SUMMARY OF THE INVENTION

Preferred embodiments of the present invention provide pulse wave transit time measurement devices capable of continuously measuring a pulse wave transit time with higher stability even when a posture of a user is changed during measurement of the pulse wave transit time, and living body state estimation devices including the pulse wave transit time measurement devices.

A pulse wave transit time measurement device according to a preferred embodiment of the present invention includes an electrocardiographic electrode that detects an electrocardiographic signal, a pulse wave sensor that detects a pulse wave signal, and a pulse wave transit time calculator that calculates a pulse wave transit time based on a peak time difference between the electrocardiographic signal detected by the electrocardiographic electrodes and the pulse wave signal detected by the pulse wave sensor, wherein the pulse wave sensor is positioned in contact with a neck of a user at or near a midline of the neck when the pulse wave transit time is determined by the pulse wave transit time calculator.

With a pulse wave transit time measurement device according to a preferred embodiment of the present invention, when the pulse wave transit time is calculated, the pulse wave sensor is held in contact with the neck of the user near the midline of the neck. The pulse wave transit time is then calculated from the pulse wave signal detected near the midline of the neck. Therefore, fluctuations in the pulse wave transit time with respect to changes of the posture (including, for example, the left and right lateral decubitus positions, and the supine position) are able to be reduced as compared to the case of obtaining the pulse wave signal at a location other than the vicinity of the midline of the neck, for example, at the left or the right of the neck. Thus, the fluctuations in the pulse wave transit time are able to be reduced and a measured value is able to be stabilized even in a situation in which the posture of the user is frequently changed (for example, when the user rolls over in sleep). As a result, the pulse wave transit time is able to be continuously calculated with higher stability even when the posture of the user is changed during the measurement of the pulse wave transit time.

In a pulse wave transit time measurement device according to a preferred embodiment of the present invention, the pulse wave sensor is preferably positioned in contact with the neck of the user at or near the midline of the neck on the backside when the pulse wave transit time is calculated.

In this case, when the pulse wave transit time is calculated, the pulse wave sensor is held in contact with the neck of the user near the midline on the backside. Therefore, the pulse wave sensor is able to be set more easily without causing the user to feel discomfort than the case in which the pulse wave sensor is held in contact with the neck near the midline on the front side. In addition, a contact state of the pulse wave sensor with the neck surface is able to be made more stable.

Preferably, a pulse wave transit time measurement device according to a preferred embodiment of the present invention further includes a wearable member capable of being set around the neck of the user in a circumferential direction, a surface of the pulse wave sensor is flush or substantially flush with a surface of the wearable member, and the pulse wave sensor is positioned in or substantially in a central region of the wearable member at a location at which the pulse wave sensor is held in contact with the neck of the user at or near the midline of the neck on the backside when the wearable member is set around the neck of the user.

In this case, the surface of the pulse wave sensor is flush or substantially flush with the surface of the wearable member. In other words, the pulse wave sensor does not project from the surface of the wearable member. Therefore, even when the back of the neck is in contact with the pulse wave sensor in the supine position, for example, the user does not feel pain. Furthermore, since the surface of the pulse wave sensor is not recessed, the skin of the neck on the backside is able to be surely brought into close contact with the pulse wave sensor, and the pulse wave transit time is able to be measured more stably.

Preferably, a pulse wave transit time measurement device according to a preferred embodiment of the present invention further includes a posture detector that detects a posture of the user when the pulse wave transit time is calculated by the pulse wave transit time calculator, a classifier that classifies time serial data of the calculated pulse wave transit time for each posture depending on the posture detected by the posture detector, and a fluctuation identifier that determines fluctuations in the pulse wave transit time based on the time serial data of the pulse wave transit time having been classified for each posture by the classifier.

In this case, the time serial data of the calculated pulse wave transit time is classified for each posture, and the fluctuations in the pulse wave transit time are determined based on the time serial data of the pulse wave transit time having been classified for each posture. Therefore, it is possible to determine, for each posture, whether obtained data (i.e., the time serial data of the pulse wave transit time) is to be used or not, and to correct the obtained data. As a result, even when the posture of the user is changed during the measurement of the pulse wave transit time, the fluctuations in the pulse wave transit time are able to be continuously determined with higher stability.

In a pulse wave transit time measurement device according to a preferred embodiment of the present invention, preferably, the fluctuation identifier sets a reference posture from among the classified postures, corrects, in conformity with the reference posture, the time serial data of the pulse wave transit time having been classified into the posture different from the reference posture, and determines the fluctuations in the pulse wave transit time based on both of the time serial data of the pulse wave transit time in the reference posture and the time serial data of the pulse wave transit time having been corrected.

In this case, the reference posture is set from among the classified postures, and the time serial data of the pulse wave transit time having been classified into the posture different from the reference posture is corrected in conformity with the reference posture. The fluctuations in the pulse wave transit time are then determined based on both of the time serial data of the pulse wave transit time in the reference posture and the time serial data of the pulse wave transit time having been corrected (after the correction). In other words, when the posture of the user is changed during the measurement of the pulse wave transit time, the time serial data of the pulse wave transit time having been classified into the posture different from the reference posture is corrected in conformity with the reference posture (namely, to provide the time serial data based on the assumption that the relevant time serial data is obtained in the reference posture). As a result, even when the posture of the user is changed during the measurement of the pulse wave transit time, the fluctuations in the pulse wave transit time are able to be continuously determined with higher stability.

In a pulse wave transit time measurement device according to a preferred embodiment of the present invention, preferably, the fluctuation identifier sets, as the reference posture, the posture in which a time span of the time serial data of the calculated pulse wave transit time is longest.

In this case, the posture in which the time span of the time serial data of the calculated pulse wave transit time is longest is set as the reference posture. Therefore, a ratio of the time serial data requiring the correction to all of the time serial data of the calculated pulse wave transit time is able to be reduced. As a result, the fluctuations in the pulse wave transit time are able to be determined with higher accuracy, and a processing load required for the correction is able to be reduced.

In a pulse wave transit time measurement device according to a preferred embodiment of the present invention, preferably, the fluctuation identifier corrects the time serial data of the pulse wave transit time for each posture such that a correlation coefficient of an approximation curve resulting from approximating the time serial data of the pulse wave transit time for each posture with a curve is increased, and determines the fluctuations in the pulse wave transit time from the time serial data after the correction.

In this case, the time serial data of the pulse wave transit time for each posture is corrected such that the correlation coefficient of the approximation curve is increased. The fluctuations in the pulse wave transit time are then determined from the time serial data after the correction. Therefore, the time serial data of the pulse wave transit time having been classified into the posture different from the reference posture is able to be appropriately corrected in conformity with the reference posture (namely, in such a manner as to provide the time serial data on the assumption that the relevant time serial data is obtained in the reference posture).

In a pulse wave transit time measurement device according to a preferred embodiment of the present invention, preferably, the fluctuation identifier determines the fluctuations in the pulse wave transit time based on, among all of the classified time serial data of the pulse wave transit time, only the time serial data of the pulse wave transit time corresponding to a predetermined posture.

In this case, the fluctuations in the pulse wave transit time are determined based on, among all of the classified time serial data of the pulse wave transit time, only the time serial data of the pulse wave transit time corresponding to the predetermined posture. Thus, when the posture of the user is changed during the measurement of the pulse wave transit time, the fluctuations in the pulse wave transit time are determined after excluding, from the obtained data, the time serial data of the pulse wave transit time having been classified into the posture different from the predetermined posture. As a result, the fluctuations in the pulse wave transit time are able to be accurately determined even when the posture of the user is changed during the measurement of the pulse wave transit time.

In a pulse wave transit time measurement device according to a preferred embodiment of the present invention, preferably, the classifier classifies the time serial data of the pulse wave transit time for each of the postures including at least an upright position, an inverted position, a supine position, a left lateral decubitus position, a right lateral decubitus position, and a prone position.

In this case, the time serial data of the pulse wave transit time is classified for each of the postures including at least the upright position, the inverted position, the supine position, the left lateral decubitus position, the right lateral decubitus position, and the prone position. Therefore, the posture during the measurement of the pulse wave transit time is able to be classified more precisely. In trying to check, for example, a trend of the fluctuations in the pulse wave transit time during sleep of the user, the time serial data of the pulse wave transit time is able to be more appropriately corrected even when the posture of the user is changed (for example, even when the user rolls over in sleep), and the fluctuations in the pulse wave transit time are able to be continuously determined with higher stability.

In a pulse wave transit time measurement device according to a preferred embodiment of the present invention, preferably, the posture detector includes an acceleration sensor that detects a direction in which a gravitational acceleration is applied, and the pulse wave sensor and the acceleration sensor are disposed adjacent to or in a vicinity of each other.

In this case, the pulse wave sensor and the acceleration sensor are positioned on the neck (nape) of the user close to each other. Therefore, the posture of a portion of a body at which the pulse wave transit time is measured is able to be accurately determined, and the correlation between the determination of the posture and the pulse wave transit time is increased.

A living body state estimation device according to a preferred embodiment of the present invention includes any of the pulse wave transit time measurement devices described above, and a blood pressure fluctuation estimator that estimates fluctuations in blood pressure based on both data of the fluctuations in the calculated pulse wave transit time and a predetermined relationship between the pulse wave transit time and a blood pressure.

With a living body state estimation device according to a preferred embodiment of the present invention, due to the inclusion of any of the pulse wave transit time measurement devices described above, the fluctuations in the pulse wave transit time are able to be continuously determined with higher stability even when the posture of the user is changed during the measurement of the pulse wave transit time. Thus, the fluctuations in the blood pressure are able to be continuously estimated with higher stability even when the posture of the user is changed during the measurement of the pulse wave transit time (for example, even when the user rolls over in sleep).

In a pulse wave transit time measurement device according to a preferred embodiment of the present invention, preferably, the blood pressure fluctuation estimator previously performs calibration of a relationship between an output signal of a posture detector and the posture of the user, determines a relational expression between a deviation in angle from a reference posture and a distance from a heart to a pulse-wave measurement location, and stores the relational expression; when measuring the pulse wave transit time, the blood pressure fluctuation estimator calculates, based on a result of the calibration, a deviation in angle between the posture of the user and the reference posture; and when calculating a value of blood pressure from the pulse wave transit time, the blood pressure fluctuation estimator determines the distance from the heart to the pulse-wave measurement location based on both of the calculated deviation in angle and the relational expression stored in advance, and corrects the value of the blood pressure depending on the determined distance.

The pulse wave transit time greatly fluctuates depending on the distance from the heart of the location at which the pulse wave signal is obtained, and it fluctuates even with slight changes of the posture. In the above-described case, however, when the pulse wave transit time is measured, the deviation in angle between the posture of the user and the reference posture is calculated based on the result of the calibration performed in advance. When the value of the blood pressure is calculated from the pulse wave transit time, the distance from the heart to the pulse-wave measurement location is determined based on both of the calculated deviation in angle and the relational expression stored in advance, and the value of the blood pressure is corrected depending on the determined distance. Thus, the value of the blood pressure is able to be more accurately estimated by finely calculating the deviation angle from the reference posture in addition to a major change of the posture (such as the above-mentioned six postures).

According to preferred embodiments of the present invention, the pulse wave transit time is able to be continuously calculated with higher stability even when the posture of the user is changed during the measurement of the pulse wave transit time.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
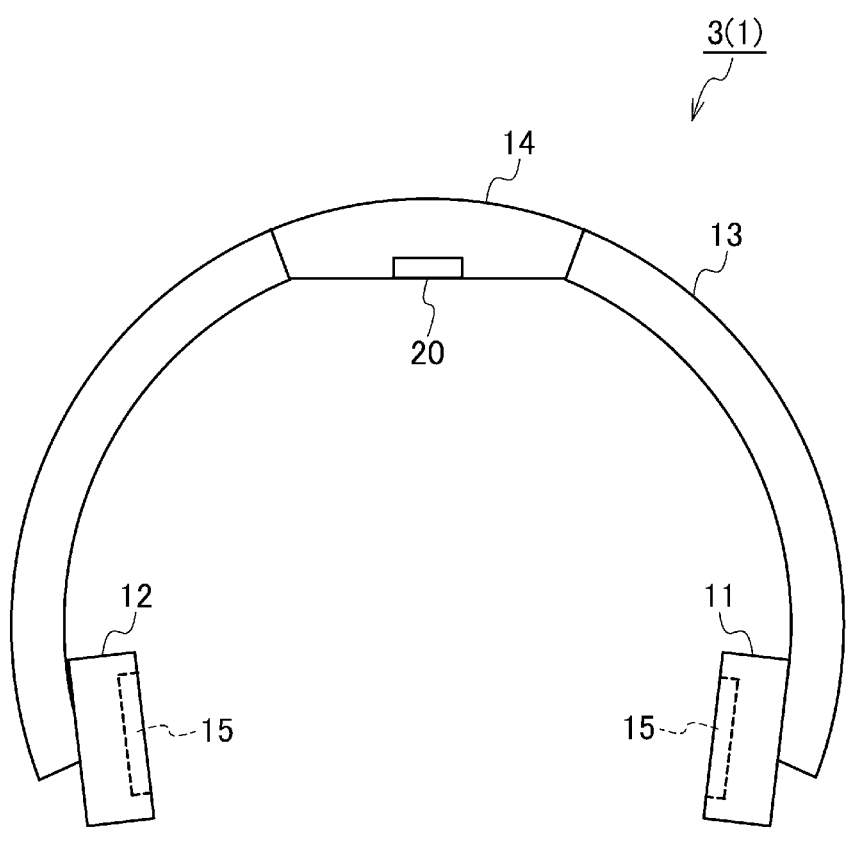
FIG. 1 is a plan view illustrating an external appearance of a blood pressure fluctuation estimation device of a neck band type including a pulse wave transit time measurement device according to a preferred embodiment of the present invention.

Preferred embodiments of the present invention will be described in detail below with reference to the drawings. In the drawings, the same or equivalent components are denoted by the same reference signs. Furthermore, the same elements are denoted by the same reference signs in the drawings, and duplicate explanation of the same elements is omitted. The following description is provided in connection with a case in which a pulse wave transit time measurement device is applied to a blood pressure fluctuation estimation device (corresponding to "a living body state estimation device").

Figure 2:
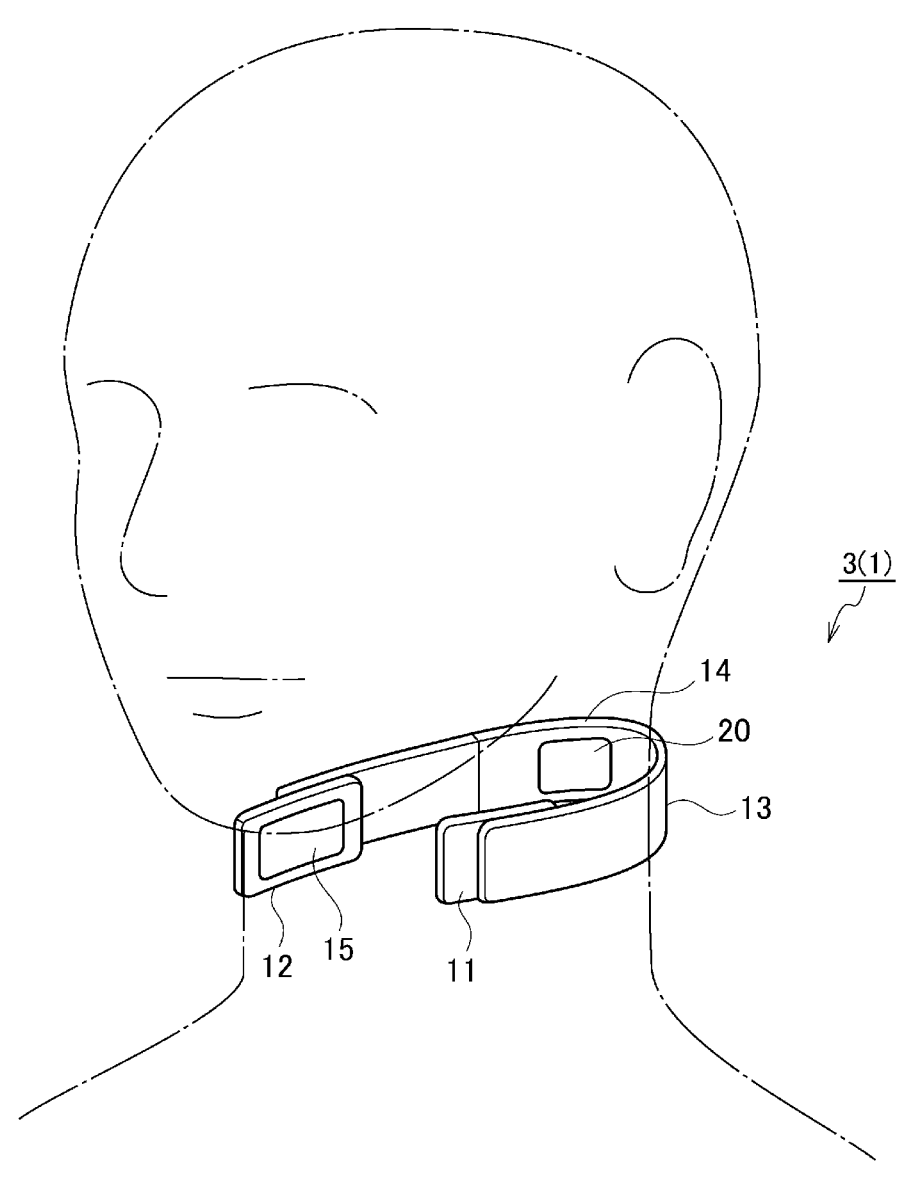
FIG. 2 is a perspective view illustrating an external appearance of a blood pressure fluctuation estimation device of a neck band type including a pulse wave transit time measurement device according to a preferred embodiment of the present invention.
Figure 3:
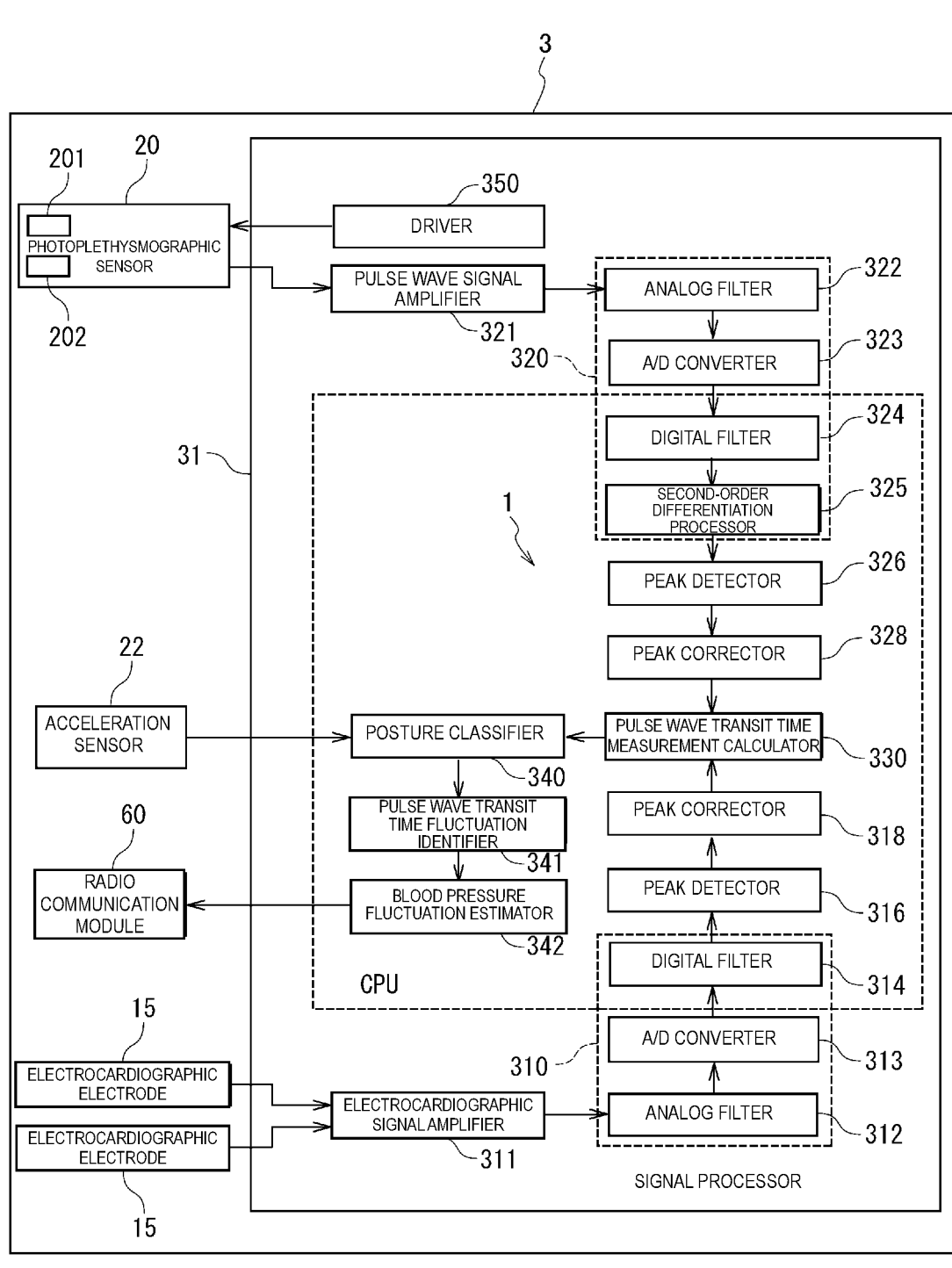
FIG. 3 is a block diagram illustrating a configuration of a blood pressure fluctuation estimation device including a pulse wave transit time measurement device according to a preferred embodiment of the present invention.

First, a configuration of a blood pressure fluctuation estimation device 3 including a pulse wave transit time measurement device 1 according to a preferred embodiment is described with reference to FIGS. 1 to 3. FIG. 1 is a plan view illustrating an external appearance of the blood pressure fluctuation estimation device 3 of neck band type including the pulse wave transit time measurement device 1. FIG. 2 is a perspective view illustrating the external appearance of the blood pressure fluctuation estimation device 3 of neck band type using the pulse wave transit time measurement device 1. FIG. 3 is a block diagram illustrating the configuration of the blood pressure fluctuation estimation device 3 using the pulse wave transit time measurement device 1.

The blood pressure fluctuation estimation device 3 detects an electrocardiographic signal and a photoplethysmographic signal, measures a pulse wave transit time from a time difference between an R-wave peak of the detected electrocardiographic signal (electrocardiographic wave) and a peak (rising point) of the detected photoplethysmographic signal (pulse wave), and estimates fluctuations in blood pressure of a user based on time serial data of the measured pulse wave transit time. In particular, the blood pressure fluctuation estimation device 3 includes a function of continuously calculating the pulse wave transit time with higher stability even when a posture of the user is changed during the measurement of the pulse wave transit time. The blood pressure fluctuation estimation device 3 further includes the functions of detecting and classifying postures of the user, correcting the pulse wave transit time in accordance with a classification result, and estimating the fluctuations in the blood pressure based on the time serial data of the pulse wave transit time after the correction.

The blood pressure fluctuation estimation device 3 primarily includes a pair of electrocardiographic electrodes 15 and 15 that detect the electrocardiographic signal, a photoplethysmographic sensor 20 that detects the photoplethysmographic signal, an acceleration sensor 22 that detects the posture of the user, and a signal processor 31 configured or programmed to measure and correct the pulse wave transit time from both of the detected electrocardiographic signal and photoplethysmographic signal, and further to estimate the fluctuations in the blood pressure.

In the present preferred embodiment, as illustrated in FIGS. 1 and 2, the blood pressure fluctuation estimation device 3 is a neck band type. The blood pressure fluctuation estimation device 3 is worn on the neck (nape) as illustrated in FIG. 2, by way of example, to calculate the time serial data of the pulse wave transit time and to estimate the fluctuations in the blood pressure. The blood pressure fluctuation estimation device 3 includes a neck band 13 (corresponding to "a wearable member") preferably having a U-shape or substantial U-shape (or a C-shape or substantial C-shape), for example, and worn around the neck of the user from the backside in a state grasping the neck with the aid of elastic force, sensors 11 and 12 disposed at both ends of the neck band 13 to be held in contact with both lateral sides of the user's neck, and a sensor 14 disposed in a central region of the neck band 13 to be held in contact with a midline of the user's neck on the backside.

The neck band 13 is wearable around the neck of the user in a circumferential direction. In other words, as illustrated in FIG. 2, the neck band 13 is worn around the back of the user's neck from one lateral side to the other lateral side of the neck. More specifically, the neck band 13 includes, for example, a band-shaped leaf spring, and a rubber coating coated around the leaf spring. Thus, the neck band 13 is biased inward in opposing directions such that, when the user wears the neck band 13, the neck band 13 (specifically, the sensors 11, 12 and 14) is held in contact with the user's neck.

The rubber coating used in the neck band preferably has biocompatibility. A coating made of plastic, for example, may also be used, instead of the rubber coating. Cables providing electrical connection of the sensors 11, 12 and 14 are provided in the rubber coating. The cables are preferably coaxial cables, for example, from the viewpoint of reducing noise.

The sensors 11 and 12 respectively include a pair of the electrocardiographic electrodes 15 and 15. The electrocardiographic electrode 15 may preferably be made of, for example, silver—silver chloride, conductive gel, conductive rubber, conductive plastic, a metal (preferably being highly resistant to corrosion and less metal-allergic, such as stainless or Au), a conductive cloth, or a capacitive coupling electrode including a metal surface coated with an insulating layer. The conductive cloth may be, for example, a woven fabric, a knit fabric, or an unwoven fabric made using conductive fibers with electrical conductivity. The conductive fibers may be, for example, resin fibers plated with a metal. such as Ag, coated with carbon nanotubes, or coated with a conductive polymer such as PEDOT. Alternatively, a conductive polymer fiber with electrical conductivity may also be used. In the present preferred embodiment, for example, a conductive cloth 15 having a rectangular or substantially rectangular plan shape is preferably used as the electrocardiographic electrode 15. The pair of electrocardiographic electrodes 15 and 15 is connected to the signal processor 31 and outputs the electrocardiographic signal to the signal processor 31.

The acceleration sensor 22 that detects a posture of the user (neck) during the measurement of the pulse wave transit time is attached to the sensor 14. Thus, the acceleration sensor 22 defines and functions as "a posture detector". The acceleration sensor 22 is preferably a 3-axis acceleration sensor that detects a direction in which a gravitational acceleration G is applied (i.e., a vertical direction). For example, whether the user is standing or lying is able to be determined from a detected signal of the acceleration sensor 22.

More specifically, the posture of the user is able to be determined by previously performing calibration with respect to a positional relationship between a body of the user and the acceleration sensor 22, and by performing coordinate transformation of an output of the acceleration sensor 22 on the assumption that the direction in which the gravitational acceleration is applied represents a downward direction (vertical direction), for example. The acceleration sensor 22 is also connected to the signal processor 31 and outputs a detected signal (3-axis acceleration data) to the signal processor 31. A gyroscope sensor, for example, may also be used, instead of the acceleration sensor 22.

The photoplethysmographic sensor 20 including a light emitting element 201 and a light receiving element 202 and detecting the photoplethysmographic signal is disposed at an inner surface (i.e., a surface brought into contact with the neck) of the sensor 14 near the acceleration sensor 22. The photoplethysmographic sensor 20 is a sensor that optically detects the photoplethysmographic signal by utilizing light absorption characteristics of blood hemoglobin.

As described above, the sensor 14 (i.e., the photoplethysmographic sensor 20) is disposed in or substantially in the central region of the neck band 13. Therefore, the photoplethysmographic sensor 20 (i.e., the sensor 14) is structured to be positioned in contact with the neck at the midline (or the vicinity thereof) of the user's neck on the backside when the neck band 13 is worn around the user's neck, and when the pulse wave transit time is measured. The photoplethysmographic sensor 20 is structured such that a surface of the photoplethysmographic sensor 20 is flush or substantially in flush with the surface of the neck band 13.

The photoplethysmographic sensor 20 and the acceleration sensor 22 are disposed close to each other and are set on the neck (nape) of the user when in use (i.e., during the measurement). Since the photoplethysmographic sensor 20 and the acceleration sensor 22 that determine the posture are set at the same or substantially the same location as described above, correlation between the determination of the posture and the pulse wave transit time is increased. Furthermore, since those sensors are set on the neck instead of a hand or a leg, for example, a blood pressure within blood vessels in the neck, which is thought as having relatively high correlation to the risk of cerebral stroke, cardiac infarction, etc., is able to be estimated instead of a blood pressure within blood vessels in the hand or the leg. In addition, since the plurality of sensors are collectively set on the neck without being set at separate locations, the complexity in setting the plurality of sensors is reduced, and restrictions on daily activity of the user are also reduced. The acceleration sensor 22 is preferably disposed near the photoplethysmographic sensor 20, but it may be arranged at another location inside the device as long as a structure in which a relative position with respect to the photoplethysmographic sensor 20 is not changed.

The light emitting element 201 emits light in response to a pulse-shaped drive signal output from a driver 350 in the signal processor 31 described later. The light emitting element 201 may preferably be, for example, an LED, a VCSEL (Vertical Cavity Surface Emitting LASER), or a resonator type LED. The driver 350 is configured or programed to produce and output the pulse-shaped drive signal to drive the light emitting element 201.

The light receiving element 202 outputs a detected signal depending on the intensity of the light emitted from the light emitting element 201 and coming into the light receiving element 202 after passing through the neck or being reflected by the neck. The light receiving element 202 is preferably a photodiode or a phototransistor, for example. In the present preferred embodiment, a photodiode is used as the light receiving element 202.

The light receiving element 202 is connected to the signal processor 31, and the detected signal (photoplethysmographic signal) from the light receiving element 202 is output to the signal processor 31.

A battery (not illustrated) supplying electric power to the photoplethysmographic sensor 20, the signal processor 31, a radio communication module 60, and other components is included inside the sensor 11. The signal processor 31 and the radio communication module 60 configured or programmed to transmit biological information, such as the fluctuations in the blood pressure, the measured pulse wave transit time, the electrocardiographic signal, and the photoplethysmographic signal, to an external device are included inside the sensor 12.

As described above, the pair of electrocardiographic electrodes 15 and 15 and the photoplethysmographic sensor 20 are connected to the signal processor 31 such that the detected electrocardiographic signal and the detected photoplethysmographic signal are input to the signal processor 31. The acceleration sensor 22 is also connected to the signal processor 31 such that the detected 3-axis acceleration signal is input to the signal processor 31.

The signal processor 31 processes the input electrocardiographic signal and measures a heart rate, a heartbeat interval, and other parameters, for example. The signal processor 31 further processes the input photoplethysmographic signal and measures a pulse rate, a pulse interval, and other parameters, for example. In addition, the signal processor 31 measures the pulse wave transit time from a time difference between an R-wave peak of the detected electrocardiographic signal (electrocardiographic wave) and a peak (rising point) of the detected photoplethysmographic signal (acceleration pulse wave signal). Thereafter, the signal processor 31 estimates the fluctuations in the blood pressure of the user from the time serial data (fluctuations) of the measured pulse wave transit time.

To that end, the signal processor 31 includes an electrocardiographic signal amplifier 311, a pulse wave signal amplifier 321, a first signal processor 310, a second signal processor 320, peak detectors 316 and 326, peak correctors 318 and 328, a pulse wave transit time calculator 330, a posture classifier 340, a pulse wave transit time fluctuation identifier 341, and a blood pressure fluctuation estimator 342. The first signal processor 310 includes an analog filter 312, an A/D converter 313, and a digital filter 314. The second signal processor 320 includes an analog filter 322, an A/D converter 323, a digital filter 324, and a second-order differentiation processor 325.

Among the above-described components and elements, the digital filters 314 and 324, the second-order differentiation processor 325, the peak detectors 316 and 326, the peak correctors 318 and 328, the pulse wave transit time measurement calculator 330, the posture classifier 340, the pulse wave transit time fluctuation identifier 341, and the blood pressure fluctuation estimator 342 are preferably defined by a CPU, or two or more CPUs, configured or programmed to execute arithmetic processing, a ROM storing programs and data necessary to operate the CPU to execute various types of processing, and a RAM temporarily storing various data, such as calculation results. In other words, the functions of the above-described components and elements are implemented with the CPU, or CPUs, executing the programs stored in the ROM.

The electrocardiographic signal amplifier 311 is preferably defined by an amplifier using an operational amplifier, for example, and it amplifies the electrocardiographic signal detected by the pair of electrocardiographic electrodes (conductive clothes) 15 and 15. The electrocardiographic signal amplified by the electrocardiographic signal amplifier 311 is output to the first signal processor 310. Similarly, the pulse wave signal amplifier 321 is preferably defined by an amplifier using an operational amplifier, for example, and it amplifies the photoplethysmographic signal detected by the photoplethysmographic sensor 20. The photoplethysmographic signal amplified by the pulse wave signal amplifier 321 is output to the second signal processor 320.

The first signal processor 310 includes the analog filter 312, the A/D converter 313, and the digital filter 314 as described above, and extracts a pulsatile component by executing a filtering process on the electrocardiographic signal amplified by the electrocardiographic signal amplifier 311.

The second signal processor 320 includes the analog filter 322, the A/D converter 323, the digital filter 324, and the second-order differentiation processor 325 as described above, and extracts a pulsatile component by executing a filtering process and a second-order differentiation process on the photoplethysmographic signal amplified by the pulse wave signal amplifier 321.

The analog filters 312 and 322 and the digital filters 314 and 324 perform filtering to remove components (noise) at frequencies other than the frequencies of the electrocardiographic signal and the photoplethysmographic signal, and to increase the S/N ratio. More specifically, because frequency components from about 0.1 Hz to about 200 Hz are typically dominant in the electrocardiographic signal and frequency components from about 0.1 Hz to about several tens Hz are typically dominant in the photoplethysmographic signal, the S/N ratio is increased by using the analog filters 312 and 322 and the digital filters 314 and 324, which are preferably, for example, low pass filters or band pass filters, to perform the filtering process such that only signals in the above-described frequency ranges selectively pass through the filters.

In the case of extracting only the pulsatile component, components other than the pulsatile component may be cut by more restrictively narrowing a frequency pass band to improve noise immunity. Both types of the analog filters 312 and 322 and the digital filters 314 and 324 are not always required to be provided, and the configuration may be modified to include only one type of the analog filters 312 and 322 and the digital filters 314 and 324. The electrocardiographic signal having been subjected to the filtering process through the analog filter 312 and the digital filter 314 is output to the peak detector 316. Similarly, the photoplethysmographic signal having been subjected to the filtering process through the analog filter 322 and the digital filter 324 is output to the second-order differentiation processor 325.

The second-order differentiation processor 325 obtains a second-order differentiation pulse wave (acceleration pulse wave) signal through second-order differentiation of the photoplethysmographic signal. The obtained acceleration pulse wave signal is output to the peak detector 326. Because change of a peak (rising point) of a photoplethysmographic pulse wave is not definite and is difficult to detect in some cases, the peak is preferably detected after converting the photoplethysmographic pulse wave to an acceleration pulse wave. However, the second-order differentiation processor 325 is not always required to be provided, and it may be omitted in another configuration.

The peak detector 316 detects the peak (R-wave) of the electrocardiographic signal on which the signal processing has been executed in the first signal processor 310 (namely, from which the pulsatile component has been extracted). On the other hand, the peak detector 326 detects the peak of the photoplethysmographic signal (acceleration pulse wave) on which the filtering process has been executed in the second signal processor 320. The peak detector 316 and the peak detector 326 perform the peak detection within normal ranges of the heartbeat interval and the pulse interval, and store information, such as peak time and peak amplitude, for all of the detected peaks in the RAM, for example.

The peak corrector 318 determines a delay time of the electrocardiographic signal caused in the first signal processor 310 (i.e., the analog filter 312, the A/D converter 313, and the digital filter 314). Based on the determined delay time of the electrocardiographic signal, the peak corrector 318 corrects the peak of the electrocardiographic signal, which has been detected by the peak detector 316. Similarly, the peak corrector 328 determines a delay time of the photoplethysmographic signal caused in the second signal processor 320 (i.e., the analog filter 322, the A/D converter 323, the digital filter 324, and the second-order differentiation processor 325). Based on the determined delay time of the photoplethysmographic signal, the peak corrector 328 corrects the peak of the photoplethysmographic signal, which has been detected by the peak detector 326. The peak of the electrocardiographic signal after the correction and the peak of the photoplethysmographic signal (acceleration pulse wave) after the correction are output to the pulse wave transit time calculator 330. The peak corrector 318 is not always required to be provided, and it may be omitted in another configuration.

The pulse wave transit time calculator 330 time-serially calculates a pulse wave transit time from an interval (time difference) between the R-wave peak of the electrocardiographic signal having been corrected by the peak corrector 318 and the peak of the photoplethysmographic signal (acceleration pulse wave) having been corrected by the peak corrector 328. Thus, the pulse wave transit time calculator 330 defines and functions as "a pulse wave transit time identifier".

The pulse wave transit time calculator 330 calculates, in addition to the pulse wave transit time, the heart rate, the heartbeat interval, a change rate of the heartbeat interval, and other parameters from the electrocardiographic signal. Similarly, the pulse wave transit time calculator 330 further calculates the pulse rate, the pulse interval, a change rate of the pulse interval, and other parameters from the photoplethysmographic signal (acceleration pulse wave). The time serial data of the pulse wave transit time is output to the posture classifier 340.

The posture classifier 340 determines (estimates) the posture of the user based on the detected signal from the acceleration sensor 22 (i.e., the 3-axis acceleration data), and classifies the time serial data of the pulse wave transit time for each posture depending on the determined posture. More specifically, the posture classifier 340 classifies the time serial data of the pulse wave transit time for each of postures including at least an upright position, an inverted position, a supine position, a left lateral decubitus position, a right lateral decubitus position, and a prone position. Thus, the posture classifier 340 defines and functions as "a classifier".

Figure 4:
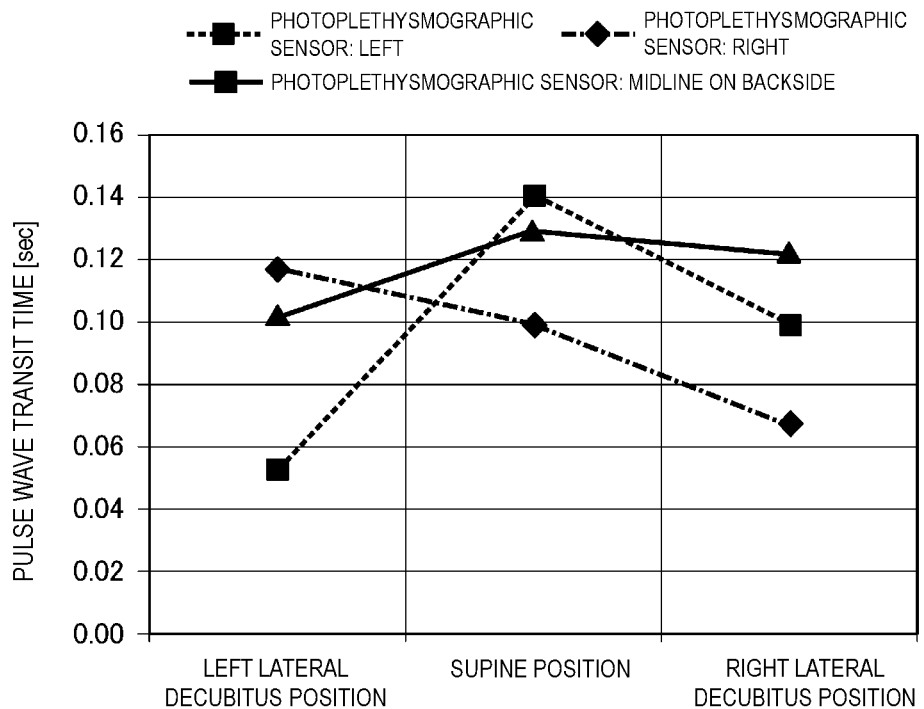
FIG. 4 is a graph depicting relationships among measurement locations, postures (supine position, left lateral decubitus position, and right lateral decubitus position), and a pulse wave transit time.

FIG. 4 depicts relationships among measurement locations (i.e., a left lateral surface of the neck, a right lateral surface of the neck, and a midline of the neck on the backside), the postures (i.e., the supine position, the left lateral decubitus position, and the right lateral decubitus position), and the pulse wave transit time. As illustrated in FIG. 4, when the photoplethysmographic sensor 20 is set on the left side of the neck (nape) (see a dotted line), the pulse wave transit time is shortened in the left lateral decubitus position (as compared to that in each of the right lateral decubitus position and the supine position). On the other hand, when the photoplethysmographic sensor 20 is set on the right side of the neck (nape) (see a one-dot-chain line), the pulse wave transit time is shortened in the right lateral decubitus position (compared to that in each of the left lateral decubitus position and the supine position). Those results are attributable to the fact that the blood pressure is increased and the pulse wave transit time is shortened in the position in which the measurement location is on the lower side.

Compared to the above two cases, dependency of the pulse wave transit time upon the posture is reduced when the photoplethysmographic sensor 20 is at or near the midline of the neck on the backside (see a solid line). In other words, fluctuations in the pulse wave transit time are reduced even when the posture is changed. This is attributable to the fact that, when the photoplethysmographic sensor 20 is at or near the midline of the neck on the backside, change of distance relative to the heart resulting from change of the posture (i.e., the supine position, the left lateral decubitus position, and the right lateral decubitus position) is reduced. Thus, in the case of wearing the blood pressure fluctuation estimation device 3 around the neck (nape) as illustrated in FIG. 2, for example, change of the pulse wave transit time depending on the change of the posture is smaller when the pulse wave transit time is measured at or near the midline of the neck on the backside than when the pulse wave transit time is measured at the left or right of the neck. A classification result of the pulse wave transit time obtained by the posture classifier 340 (i.e., the classified time serial data of the pulse wave transit time) is output to the pulse wave transit time fluctuation identifier 341.

The pulse wave transit time fluctuation identifier 341 determines fluctuations in the pulse wave transit time based on the time serial data of the pulse wave transit time having been classified for each posture by the posture classifier 340. Thus, the pulse wave transit time fluctuation identifier 341 defines and functions as "a fluctuation identifier".

In more detail, the pulse wave transit time fluctuation identifier 341 first sets one posture (e.g., the supine position) as a reference from among the classified postures, and corrects, in conformity with the reference posture, the time serial data of the pulse wave transit time having been classified into the postures (e.g., the upright position, the inverted position, the left lateral decubitus position, the right lateral decubitus position, and the prone position) different from the reference posture. Then, the pulse wave transit time fluctuation identifier 341 determines the fluctuations in the pulse wave transit time based on both of the time serial data of the pulse wave transit time in the reference posture and the time serial data of the pulse wave transit time having been corrected (after the correction).

At this time, the pulse wave transit time fluctuation identifier 341 sets, as the reference posture, the posture (e.g., the supine position) in which a time span of the time serial data of the calculated pulse wave transit time is longest. Then, the pulse wave transit time fluctuation identifier 341 corrects the time serial data of the pulse wave transit time for each posture such that a correlation coefficient of an approximation curve resulting from approximating the time serial data of the pulse wave transit time for each posture with a curve is increased and preferably maximized. Furthermore, the pulse wave transit time fluctuation identifier 341 determines the fluctuations in the pulse wave transit time from the time serial data after the correction. Thus, by correcting the pulse wave transit time for each posture by increasing the correlation coefficient of the approximation curve and estimating a trend of the fluctuations in the pulse wave transit time from the time serial data after the correction, the trend of the fluctuations in the pulse wave transit time (trend of the fluctuations in the blood pressure) for a long time is able to be estimated without requiring intricate calibration even when the posture is changed. For example, the least square method may be used as a method of determining the above-described approximation curve.

Instead of the above-described manner, the pulse wave transit time for each posture may be arrayed in the time series, and an approximation curve may be determined for each of the postures. In this case, although a plurality of approximation curves are determined, one of those approximation curves, the one having a greater correlation coefficient is selected from among the approximation curves corresponding to the postures in which the measurement has been performed for a time at a predetermined rate or more. The data obtained by the pulse wave transit time fluctuation identifier 341 and representing the fluctuations in the pulse wave transit time is output to the blood pressure fluctuation estimator 342.

The blood pressure fluctuation estimator 342 estimates the fluctuations in the blood pressure based on both the data of the fluctuations in the pulse wave transit time after the correction and a predetermined relationship (correlation formula) between the pulse wave transit time and the blood pressure. Thus, the blood pressure fluctuation estimator 342 defines and functions as "a blood pressure fluctuation estimator". The blood pressure fluctuation estimator 342 is able to estimate the fluctuations in the blood pressure from the fluctuations in the pulse wave transit time after the correction by estimating the fluctuations in the blood pressure with the aid of, for example, a predetermined correlation formula between the pulse wave transit time and the blood pressure in the reference posture (e.g., the supine position). The correlation formula between the pulse wave transit time and the blood pressure may be determined in the posture other than the supine position, or for each of the plurality of postures.

Furthermore, the blood pressure fluctuation estimator 342 performs, based on the estimated fluctuations in the blood pressure, classification into the dipper type, the non-dipper type, the riser type, and the extreme-dipper type. In the normal case, the fluctuations in the blood pressure exhibit the dipper type in which the blood pressure decreases during sleep. On the other hand, in the case of hypertensive patients, the blood pressure at night is relatively high or is not decreased (i.e., the riser type or the non-dipper type), and the risk of cerebral stroke, cardiac infarction, and other medical problems increases. In the case of patients taking antihypertensive drugs, the blood pressure may decrease excessively during sleep (i.e., the extreme-dipper type), and the risk of cerebral stroke, cardiac infarction, other medical problems may increase occasionally. Thus, the determination regarding the riser type, the non-dipper type, and the extreme-dipper type is able to be made by obtaining the fluctuations in the blood pressure during sleep.

The blood pressure fluctuation estimator 342 may previously perform, in a state of the user wearing the device, calibration for the determination of the posture, i.e., calibration of a relationship between the output signal (in the vertical direction) of the acceleration sensor 22 and the posture of the user (e.g., the upright position or the supine position), may determine a relational expression between a deviation in angle from the reference posture (i.e., a deviation angle) and a distance from the heart to a pulse-wave measurement location (i.e., a setting location of the photoplethysmographic sensor 20), and may store the relational expression in a memory, such as a RAM, for example. When measuring the pulse wave transit time (i.e., in use), the blood pressure fluctuation estimator 342 may calculate, based on a result of the calibration performed in advance, a deviation in angle (deviation angle) between the posture of the user detected by the acceleration sensor 22 and the reference posture. When calculating a value of blood pressure from the pulse wave transit time, the blood pressure fluctuation estimator 342 may determine the distance from the heart to the pulse-wave measurement location (i.e., the setting location of the photoplethysmographic sensor 20) based on both of the calculated deviation in angle (deviation angle) and the relational expression stored in advance, and may correct the value of the blood pressure depending on the determined distance. The value of the blood pressure is not always required to be determined.

Measurement data including not only the estimated fluctuations in the blood pressure and the value of the blood pressure, but also the calculated pulse wave transit time, the heart rate, the heartbeat interval, the pulse rate, the pulse interval, the photoplethysmographic pulse wave, the acceleration pulse wave, and the 3-axis accelerations is output to, for example, the memory, such as the RAM, or to the radio communication module 60. The measurement data may be stored in the memory to be readable together with the daily fluctuation history, or may be wirelessly transmitted in real time to an external device, such as a personal computer (PC) or a smartphone, for example. Alternatively, the measurement data may be stored in the memory inside the device during the measurement, and may be transmitted to an external device by automatically connecting the relevant device to the external device after the end of the measurement.

Figure 5:
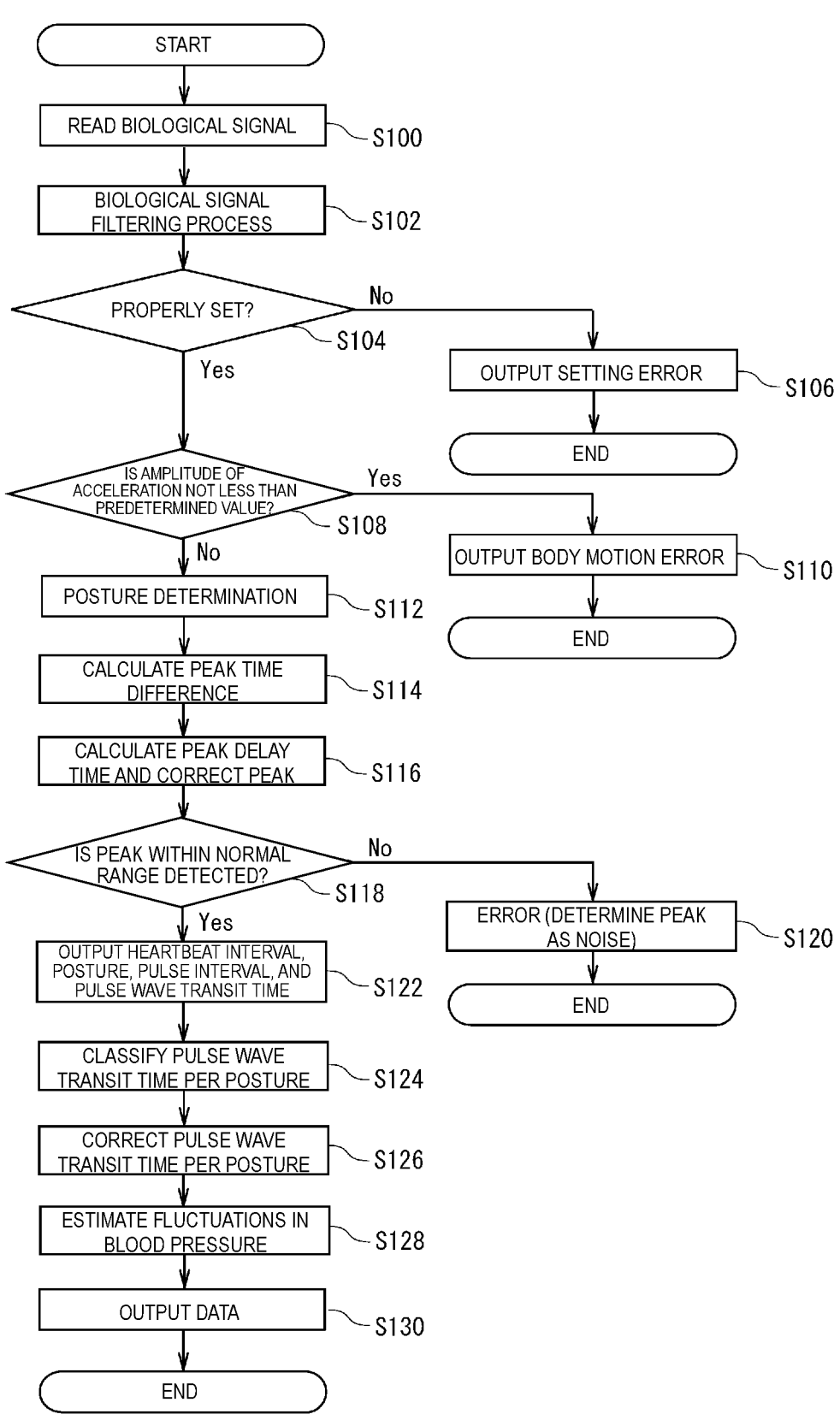
FIG. 5 is a flowchart illustrating processing procedures of a blood pressure fluctuation estimation process executed by a blood pressure fluctuation estimation device according to a preferred embodiment of the present invention.

The operation of the blood pressure fluctuation estimation device 3 will be described below with reference to FIG. 5. FIG. 5 is a flowchart illustrating processing procedures of a blood pressure fluctuation estimation process executed by the blood pressure fluctuation estimation device 3. The processing procedures illustrated in FIG. 5 are repeatedly executed at predetermined time intervals primarily by the signal processor 31.

When the blood pressure fluctuation estimation device 3 is worn around the neck such that the sensors 11 and 12 (specifically, the electrocardiographic electrodes 15 and 15) are in contact with the left and the right of the neck, respectively, and that the sensor 14 (specifically, the photoplethysmographic sensor 20) is set in contact with the midline of the neck on the backside (or the vicinity thereof), the electrocardiographic signal detected by the pair of electrocardiographic electrodes 15 and 15 and the photoplethysmographic signal detected by the photoplethysmographic sensor 20 are read in step S100. In step S102, the filtering process is performed on the electrocardiographic signal and the photoplethysmographic signal both having been read in step S100. Furthermore, an acceleration pulse wave is obtained through the second differentiation of the photoplethysmographic signal.

Then, in step S104, a setting state of the pulse wave transit time measurement device 1 is determined, for example, based on the intensity of light received by the photoplethysmographic sensor 20. More specifically, in the photoplethysmographic sensor 20, light emitted from the limit emitting element 201 and returned after passing through or being reflected by a living body is received by the light receiving element 202, and fluctuations in the intensity of the received light are detected as the photoplethysmographic signal. Therefore, the intensity of the received signal light is reduced in the state in which the device is not properly set. Taking the above point into account, in step S104, it is determined whether the intensity of the received light is not less than a predetermined value. If the intensity of the received light is not less than the predetermined value, the processing shifts to step S108. On the other hand, if the intensity of the received light is less than the predetermined value, this is determined to be a setting error, and setting error information (warning information) is output in step S106. Thereafter, the processing is brought to an end. Instead of the above-described method of utilizing the intensity of the light received by the photoplethysmographic sensor 20, the setting state may be determined by another method of utilizing, for example, the magnitude of the photoplethysmographic signal, stability of the baseline of an electrocardiographic waveform, or a rate of a noise frequency component.

In step S108, it is determined whether an acceleration of the neck detected by the acceleration sensor 22 is not less than a predetermined threshold (i.e., whether the neck is moved and body motion noise is increased). If the acceleration of the neck is less than the predetermined threshold, the processing shifts to step S112. On the other hand, if the acceleration of the neck is not less than the predetermined threshold, body motion error information is output in step S110, and the processing is then brought to an end.

In step S112, the posture of the user (measurement location) is determined based on the 3-axis acceleration data. In step S114, peaks of the electrocardiographic signal and the photoplethysmographic signal (acceleration pulse wave signal) are detected. Then, a time difference (peak time difference) between the detected R-wave peak of the electrocardiographic signal and the detected peak of the photoplethysmographic signal (acceleration pulse wave) is calculated.

In step S116, respective delay times (deviations) of the R-wave peak of the electrocardiographic signal and the peak of the photoplethysmographic signal (acceleration pulse wave) are determined, and the time difference (peak time difference) between the R-wave peak of the electrocardiographic signal and the peak of the photoplethysmographic signal (acceleration pulse wave) is corrected based on the determined delay times.

Then, in step S118, it is determined whether the peak time difference corrected in step S116 is not less than a predetermined time (e.g., about 0.01 sec). If the peak time difference is not less than the predetermined time, the processing shifts to step S122. On the other hand, if the peak time difference is less than the predetermined time, error information (indicating the peak being determined as noise) is output in step S120. Thereafter, the processing is brought to an end.

In step S122, the peak time difference calculated in step S114 is definitively determined to be the pulse wave transit time, and the pulse wave interval is obtained.

Then, in step S124, the pulse wave transit time is classified for each posture of the user. Because a method for use in classifying the pulse wave transit time is as per described above, detailed description of the method is omitted here.

In step S126, the pulse wave transit time is corrected such that the correlation coefficient of the approximation curve is maximized. Because a method for use in correcting the pulse wave transit time is as described above, detailed description of the method is omitted here.

Then, in step S128, the fluctuations in the blood pressure are estimated from the fluctuations in the pulse wave transit time after the correction. Because a method for use in estimating the fluctuations in the blood pressure is as described above, detailed description of the method is omitted here. In step S130, the obtained data of the fluctuations in the blood pressure are output to the memory or the external device, such as the smartphone, for example. Thereafter, the processing is brought to an end.

According to the present preferred embodiment, as described in detail above, when the pulse wave transit time is calculated, the photoplethysmographic sensor 20 is positioned to be in contact with the neck of the user at or near the midline of the neck. The pulse wave transit time is then calculated from the pulse wave signal detected at or near the midline of the neck. Therefore, the fluctuations in the pulse wave transit time with respect to change of the posture (including, for example, the left and right lateral decubitus positions, and the supine position) are reduced as compared to the case of obtaining the pulse wave signal at a location other than the vicinity of the midline of the neck, for example, at the left or the right of the neck. Thus, the fluctuations in the pulse wave transit time are reduced and a measured value is stabilized even in a situation in which the posture of the user is frequently changed (for example, when the user rolls over in sleep). As a result, the pulse wave transit time is able to be continuously calculated with higher stability even when the posture of the user is changed during the measurement of the pulse wave transit time.

In particular, according to the present preferred embodiment, when the pulse wave transit time is calculated, the photoplethysmographic sensor 20 is positioned to be in contact with the neck of the user at or near the midline on the backside. Therefore, the photoplethysmographic sensor 20 is able to be set more easily without causing the user to feel discomfort than in the case in which the photoplethysmographic sensor 20 is in contact with the neck at or near the midline on the front side. In addition, a contact state of the photoplethysmographic sensor 20 with the neck surface is more stable.

According to the present preferred embodiment, the surface of the photoplethysmographic sensor 20 is flush or substantially flush with the surface of the neck band 13. In other words, the photoplethysmographic sensor 20 does not project from the surface of the neck band 13. Therefore, even when the back of the neck is in contact with the photoplethysmographic sensor 20 in the supine position, for example, the user does not feel pain. Furthermore, since the surface of the photoplethysmographic sensor 20 is not recessed, the skin of the neck on the backside is brought into close contact with the photoplethysmographic sensor 20, and the pulse wave transit time is able to be measured more stably.

According to the present preferred embodiment, the time serial data of the calculated pulse wave transit time is classified for each posture, and the fluctuations in the pulse wave transit time are determined based on the time serial data of the pulse wave transit time having been classified for each posture. Therefore, the time serial data of the pulse wave transit time is able to be corrected for each posture, for example. As a result, even when the posture of the user is changed during the measurement of the pulse wave transit time, the fluctuations in the pulse wave transit time are continuously determined with higher stability. In particular, an absolute value of the pulse wave transit time greatly fluctuates depending on individual differences (in blood vessel length, arterial stiffness, level of hypertension, etc.), the posture, the distance of the pulse wave measurement location from the heart, and other factors. For this reason, intricate calibration has conventionally been essential to determine the absolute value of blood pressure. According to the present preferred embodiment, however, since the pulse wave transit time is classified for each posture and a trend of the time-dependent fluctuations in the pulse wave transit time is determined, useful information is able to be obtained without performing the intricate calibration.

In particular, according to the present preferred embodiment, the reference posture is set from among the classified postures, and the time serial data of the pulse wave transit time having been classified into the posture different from the reference posture is corrected in conformity with the reference posture. The fluctuations in the pulse wave transit time are then determined based on both of the time serial data of the pulse wave transit time in the reference posture and the time serial data of the pulse wave transit time having been corrected (after the correction). In other words, when the posture of the user is changed during the measurement of the pulse wave transit time, the time serial data of the pulse wave transit time having been classified into the posture different from the reference posture is corrected in conformity with the reference posture, that is, in such a manner to provide the time serial data on the assumption that the relevant time serial data is obtained in the reference posture. As a result, even when the posture of the user is changed during the measurement of the pulse wave transit time, the fluctuations in the pulse wave transit time are able to be continuously determined with higher stability.

In the above-described process, according to the present preferred embodiment, the posture in which a time span of the time serial data of the calculated pulse wave transit time is longest is set as the reference posture. Therefore, a ratio of the time serial data requiring the correction to all of the time serial data of the calculated pulse wave transit time is reduced. As a result, the fluctuations in the pulse wave transit time are able to be determined with higher accuracy, and a processing load required for the correction is reduced.

According to the present preferred embodiment, the time serial data of the pulse wave transit time for each posture is corrected such that the correlation coefficient of the approximation curve is increased, and preferably maximized. The fluctuations in the pulse wave transit time are then determined from the time serial data after the correction. Therefore, the time serial data of the pulse wave transit time having been classified into the posture different from the reference posture is able to be appropriately corrected in conformity with the reference posture, that is, in such a manner to provide the time serial data on the assumption that the relevant time serial data is obtained in the reference posture.

According to the present preferred embodiment, the time serial data of the pulse wave transit time is classified for each of the postures including at least the upright position, the inverted position, the supine position, the left lateral decubitus position, the right lateral decubitus position, and the prone position. Therefore, the posture during the measurement of the pulse wave transit time is able to be classified more precisely. Thus, when checking, for example, a trend of the fluctuations in the pulse wave transit time during sleep of the user, the time serial data is able to be more appropriately corrected even when the posture of the user is changed (for example, even when the user rolls over in sleep), and the fluctuations in the pulse wave transit time are able to be continuously determined with higher stability.

According to the present preferred embodiment, when using the device, the photoplethysmographic sensor 20 and the acceleration sensor 22 are positioned on the neck of the user close to each other. Therefore, the posture of a portion of a body, i.e., the neck, at which the pulse wave transit time is measured is able to be accurately determined, and the correlation between the determination of the posture and the pulse wave transit time is increased. Moreover, since the sensors are set on the neck, instead of the hand or the leg, for example, a blood pressure within blood vessels in the neck, which is thought as having relatively high correlation to the risk of cerebral stroke, cardiac infarction, and other medical problems, are able to be estimated. In addition, since the plurality of sensors are collectively set on the neck without being set at separate locations, the complexity in setting the plurality of sensors is reduced, and restrictions on daily activity of the user are also reduced.

According to the present preferred embodiment, by including the pulse wave transit time measurement device 1, even when the posture of the user is changed during the measurement of the pulse wave transit time, for example, even when the user rolls over in sleep, the fluctuations in the blood pressure are able to be continuously estimated with higher stability. As a result, according to the present preferred embodiment, the determination regarding the dipper type, the non-dipper type, the riser type, and the extreme-dipper type is able to be made, and the risk of cerebral stroke, cardiac infarction, and other medical problems is able to be estimated by measuring the fluctuations in the blood pressure during sleep, for example.

While preferred embodiments of the present invention have been described in detail above, the present invention may be various modified without being limited to the above-described preferred embodiments. For instance, while the above-described preferred embodiments have been described, by way of example, in connection with the blood pressure fluctuation estimation device 3, i.e., the pulse wave transit time measurement device 1, of the neck band type in which the neck band 13 is worn around the neck of the user, the blood pressure fluctuation estimation device may be used in a state bonded to the neck of the user on the backside over a range spanning from one lateral side of the neck to the other lateral side. Furthermore, instead of wearing the device around the neck of the user, the device may be modified into a configuration in which the electrocardiographic electrodes, the pulse wave sensor, and the 3-axis acceleration sensor are bonded to a chest region (trunk) as with a Holter monitor, for example, or a configuration of chest strap type measuring heartbeats during running. In that case, the pulse wave sensor (i.e., the photoplethysmographic sensor 20) is preferably disposed at or near a midline of the chest region (trunk).

While, in the above-described preferred embodiments, the time serial data of the pulse wave transit time for each posture is corrected such that the correlation coefficient of the approximation curve is increased, and preferably, maximized, the time serial data of the pulse wave transit time for each posture may be corrected by using a conversion table that specifies, for each posture, a relationship of change of the pulse wave transit time from that in the reference posture.

While, in the above-described preferred embodiments, the predetermined correlation formula between the pulse wave transit time and the blood pressure is used to estimate the fluctuations in the blood pressure from the fluctuations in the pulse wave transit time, a conversion table specifying a relationship between the pulse wave transit time and the blood pressure for each posture may be used instead of the correlation formula.

While the photoplethysmographic sensor is used as the pulse wave sensor in the above-described preferred embodiments, a piezoelectric pulse wave sensor may be used in another example of a preferred embodiment of the present invention. Other biological sensors, such as an oxygen saturation sensor, a sound sensor (microphone), a displacement sensor, a temperature sensor, and a humidity sensor, for example, may be further used in addition to the above-described various sensors.

While, in the above-described preferred embodiments, the time serial data of the pulse wave transit time is classified per each of six postures, i.e., the upright position, the inverted position, the supine position, the left lateral decubitus position, the right lateral decubitus position, and the prone position, the posture may be more finely classified into a larger number of positions including the above six positions.

While, in the above-described preferred embodiments, the reference posture (e.g., the supine position) is set and the time serial data of the pulse wave transit time having been classified into the posture different from the reference posture is corrected in conformity with the reference posture, the fluctuations in the pulse wave transit time may be determined, instead of using such a method, based on only a portion of all of the classified time serial data of the pulse wave transit time, the portion corresponding to the predetermined posture (e.g., the supine position). In that case, when the posture of the user is changed during the measurement of the pulse wave transit time, the fluctuations in the pulse wave transit time are determined after excluding, from the obtained data, the time serial data of the pulse wave transit time having been classified into the other postures different from the predetermined posture. As a result, the fluctuations in the pulse wave transit time are able to be accurately determined even when the posture of the user is changed during the measurement of the pulse wave transit time.

While, in the above-described preferred embodiments, the signal processor 31 executes various types of processing, such as the determination of the posture, the correction of the pulse wave transit time for each posture, and the estimation of the fluctuations in the blood pressure, the obtained data including the electrocardiographic signal, the photoplethysmographic signal, and the 3-axis accelerations may be wirelessly output to a personal computer (PC) or a smartphone, for example, and the PC or the smartphone may execute the various types of processing, such as the determination of the posture, the correction of the pulse wave transit time for each posture, and the estimation of the fluctuations in the blood pressure. In that case, the above-described data such as the correlation formula is stored in the PC or the smartphone.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A pulse wave transit time measurement device comprising:
   a neck band to be worn around a neck of a user;
   a pair of electrocardiogram electrocardiogramal;
   a pulse wave sensor that detects a pulse wave signal; and
   a pulse wave transit time calculator that calculates a pulse wave transit time based on a peak time difference between the electrocardiogramaignal detected by the electrocardiogramd the pulse wave signal detected by the pulse wave sensor; wherein
   the pair of electrocardiogramalectrodes are disposed at the tip of both ends of the neck band, facing inward in opposing directions, and adapted to be held in contact with a left lateral side and a right lateral side of the neck of the user;
   the electrocardiogramaignal is detected by only two electrocardiogra that are the pair of electrocardiogramalectrodes;
   the pulse wave transit time calculator is included inside the neck band;
   the pulse wave sensor is positioned in a central region of the neck band at a location at which the pulse wave sensor is adapted to be in contact with the neck of the user at or near a midline of the neck on a backside of the neck when the pulse wave transit time is calculated by the pulse wave transit time calculator; and
   a sensing surface of the pulse wave sensor is flush or substantially flush with a surface of the neck band, and the pulse wave sensor is adapted to be in contact with the neck of the user at or near the midline of the neck on the backside of the neck when the neck band is set around the neck of the user.

2. The pulse wave transit time measurement device according to claim 1, wherein
   the neck band is capable of being set around the neck of the user in a circumferential direction of the neck.

3. The pulse wave transit time measurement device according to claim 1, further comprising:
   a posture detector that detects a posture of the user when the pulse wave transit time is calculated by the pulse wave transit time calculator;
   a classifier that classifies time serial data of the calculated pulse wave transit time for each posture depending on the posture detected by the posture detector; and
   a fluctuation identifier that determines fluctuations in the pulse wave transit time based on the time serial data of the pulse wave transit time having been classified for each posture by the classifier.

4. The pulse wave transit time measurement device according to claim 3, wherein the fluctuation identifier sets a reference posture from among the classified postures, corrects, in conformity with the reference posture, the time serial data of the pulse wave transit time having been classified into the posture different from the reference posture, and determines the fluctuations in the pulse wave transit time based on both of the time serial data of the pulse wave transit time in the reference posture and the time serial data of the pulse wave transit time having being corrected.

5. The pulse wave transit time measurement device according to claim 4, wherein the fluctuation identifier sets, as the reference posture, the posture in which a time span of the time serial data of the calculated pulse wave transit time is longest.

6. The pulse wave transit time measurement device according to claim 4, wherein the fluctuation identifier corrects the time serial data of the pulse wave transit time for each posture such that a correlation coefficient of an approximation curve resulting from approximating the time serial data of the pulse wave transit time for each posture with a curve is increased, and determines the fluctuations in the pulse wave transit time from the time serial data after the correction.

7. The pulse wave transit time measurement device according to claim 3, wherein the fluctuation identifier determines the fluctuations in the pulse wave transit time based on, among all of the classified time serial data of the pulse wave transit time, only the time serial data of the pulse wave transit time corresponding to a predetermined posture.

8. The pulse wave transit time measurement device according to claim 3, wherein the classifier classifies the time serial data of the pulse wave transit time for each of the postures including at least an upright position, an inverted position, a supine position, a left lateral decubitus position, a right lateral decubitus position, and a prone position.

9. The pulse wave transit time measurement device according to claim 3, wherein the posture detector includes an acceleration sensor that detects a direction in which a gravitational acceleration is applied; and the pulse wave sensor and the acceleration sensor are disposed adjacent or within a vicinity of each other.

10. A living body state estimation device comprising:

the pulse wave transit time measurement device according to claim 1, and a blood pressure fluctuation estimator that estimates fluctuations in blood pressure based on both data of the fluctuations in the calculated pulse wave transit time and a predetermined relationship between the pulse wave transit time and a blood pressure.

11. The living body state estimation device according to claim 10, wherein the blood pressure fluctuation estimator previously performs calibration of a relationship between an output signal of a posture detector and the posture of the user, determines a relational expression between a deviation in angle from a reference posture and a distance from a heart to a pulse-wave measurement location, and stores the relational expression;

when measuring the pulse wave transit time, the blood pressure fluctuation estimator calculates, based on a result of the calibration, a deviation in angle between the posture of the user and the reference posture; and when calculating a value of blood pressure from the pulse wave transit time, the blood pressure fluctuation estimator determines the distance from the heart to the pulse-wave measurement location based on both of the calculated deviation in angle and the relational expression stored in advance, and corrects the value of the blood pressure depending on the determined distance.

12. The living body state estimation device according to claim 10, wherein the neck band is capable of being set around the neck of the user in a circumferential direction of the neck.

13. The living body state estimation device according to claim 10, further comprising:

a posture detector that detects a posture of the user when the pulse wave transit time is calculated by the pulse wave transit time calculator;

a classifier that classifies time serial data of the calculated pulse wave transit time for each posture depending on the posture detected by the posture detector; and a fluctuation identifier that determines fluctuations in the pulse wave transit time based on the time serial data of the pulse wave transit time having been classified for each posture by the classifier.

14. The living body state estimation device according to claim 13, wherein the fluctuation identifier sets a reference posture from among the classified postures, corrects, in conformity with the reference posture, the time serial data of the pulse wave transit time having been classified into the posture different from the reference posture, and determines the fluctuations in the pulse wave transit time based on both of the time serial data of the pulse wave transit time in the reference posture and the time serial data of the pulse wave transit time having being corrected.

15. The living body state estimation device according to claim 14, wherein the fluctuation identifier sets, as the reference posture, the posture in which a time span of the time serial data of the calculated pulse wave transit time is longest.

16. The living body state estimation device according to claim 14, wherein the fluctuation identifier corrects the time serial data of the pulse wave transit time for each posture such that a correlation coefficient of an approximation curve resulting from approximating the time serial data of the pulse wave transit time for each posture with a curve is increased, and determines the fluctuations in the pulse wave transit time from the time serial data after the correction.

17. The living body state estimation device according to claim 13, wherein the fluctuation identifier determines the fluctuations in the pulse wave transit time based on, among all of the classified time serial data of the pulse wave transit time, only the time serial data of the pulse wave transit time corresponding to a predetermined posture.

18. The living body state estimation device according to claim 13, wherein the classifier classifies the time serial data of the pulse wave transit time for each of the postures including at least an upright position, an inverted position, a supine position, a left lateral decubitus position, a right lateral decubitus position, and a prone position.

* * * * *